United States Patent
Müller et al.

(10) Patent No.: US 7,109,254 B2
(45) Date of Patent: *Sep. 19, 2006

(54) METHOD FOR PRODUCING A BIOACTIVE BONE CEMENT AND BONE CEMENT KIT

(75) Inventors: Wolf-Dieter Müller, Berlin (DE); Emil Nagel, Bad Säcklngen (DE); Georg Berger, Zepernick (DE)

(73) Assignees: BAM Bundesanstalt fuer Materialforschung und - pruefung, Berlin (DE); Vita Zahnfabrik H. Rauter GmbH & Co. KG, Bad Saeckingen (DE); Humboldt-Universitaet Berlin, Charite Universitaetsklinikum (CCM) Medizinische Fakultaet der Humbolt-Universitaet, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/480,886

(22) PCT Filed: Jun. 14, 2002

(86) PCT No.: PCT/DE02/02228

§ 371 (c)(1),
(2), (4) Date: Dec. 15, 2003

(87) PCT Pub. No.: WO02/102427

PCT Pub. Date: Dec. 27, 2002

(65) Prior Publication Data

US 2004/0138759 A1   Jul. 15, 2004

(30) Foreign Application Priority Data

Jun. 15, 2001   (DE) ............................... 101 29 842

(51) Int. Cl.
*A61K 6/08*   (2006.01)
*A61K 6/83*   (2006.01)
*C08K 5/52*   (2006.01)
*C08K 3/16*   (2006.01)
*C08K 3/20*   (2006.01)
*C08K 3/22*   (2006.01)

(52) U.S. Cl. ...................... 523/105; 523/116; 524/121; 524/401; 524/413; 524/430; 524/433; 524/445

(58) Field of Classification Search ................ 523/116, 523/105; 524/121, 401, 413, 430, 433, 445
See application file for complete search history.

(56) References Cited

U.S. PATENT DOCUMENTS

| | | | | |
|---|---|---|---|---|
| 4,282,140 A | * | 8/1981 | Bousquet et al. | 523/118 |
| 4,362,510 A | * | 12/1982 | Brauer et al. | 106/35 |
| 5,747,390 A | * | 5/1998 | Cooper et al. | 442/59 |
| 5,795,922 A | * | 8/1998 | Demian et al. | 523/117 |
| 6,160,033 A | * | 12/2000 | Nies | 523/116 |
| 2004/0175409 A1 | * | 9/2004 | Muller et al. | 424/426 |

FOREIGN PATENT DOCUMENTS

| | | |
|---|---|---|
| DE | 29 06 413 | 1/1980 |
| DE | 196 41 775 | 2/1998 |
| DE | 196 35 205 A1 | 3/1998 |
| DE | 197 44 809 | 7/1999 |
| GB | 109 14 76 | 11/1967 |

* cited by examiner

*Primary Examiner*—Nathan M. Nutter
(74) *Attorney, Agent, or Firm*—Akerman Senterfitt; Stephan A. Pendorf

(57) ABSTRACT

A method for producing a bioactive bone cement and a bone cement kit for anchoring artificial joints and for filling out bone defects. The method avoids polymerization-linked by-products and disadvantageous effects, while at the same time providing the bone cement with long-term stability. The inventive method uses a monomer-free polymethylmethacrylate, which is mixed with a suitable non-toxic solvent, and a bioactive, vitreous-crystalline material with a particle size ranging from >20 to 200 μm, having 15–45 wt. % CaO, 40–45 wt. % $P_2O_5$, 10–40 wt. % $ZrO_2$ and 0.7–3.5 wt. % fluoride, having apatite and calcium zircon phosphate as main crystal phases and a glass phase as an auxiliary component until a flowable mixture is obtained. The invention also relates to a bone cement kit having said components.

10 Claims, No Drawings

METHOD FOR PRODUCING A BIOACTIVE BONE CEMENT AND BONE CEMENT KIT

FIELD OF THE INVENTION

The present invention relates to a method for producing a bioactive bone cement and a bone cement kit for anchoring artificial joints and for filling out bone defects.

BACKGROUND OF THE INVENTION

Bone cements for anchoring joints and repairing other bone defects consist of a synthetic material which as a rule is based on methylmethacrylate or related substances, in some cases with the addition of further esters of acrylic acid or methacrylic acid. Such bone cements are described e.g. in DE 196 41 775 A1. Frequently, a combination of benzoyl peroxide and dimethyl-p-toluidine is used as a catalyst in the liquid monomer, which is pointed out as a disadvantage in DE 196 35 205. Bone cements are usually prepared by mixing two components. One component contains the liquid monomer, the other is made up of a powdery polymer provided in the form of spherical particles having a diameter of approx. 100 μm.

X-ray contrast media are added for achieving the X-ray opacity required for control purposes. Known X-ray contrast media are $BaSO_4$ and $ZrO_2$, which are added in amounts ranging between 7 and 30%.

Currently, a great variety of bone cements are used, they do, however, still have disadvantages.

A general problem consists in that heat is exothermally released during polymerization. However, the bone cells which are in contact with said bone cements are damaged if the temperature rises above 50° C. The actual thermal stress put on body cells within the zone of contact with the polymerizing bone cement can only be predicted very inaccurately. It depends on the thickness of the cement layer applied, on the thermal conductivity via the prosthesis components as well as on the bone itself. Laboratory tests have shown that maximum temperatures of up to 110° C. may occur during the polymerization of commercially available cements under certain conditions, causing burns as a consequence. Improvements seem to be necessary in this respect.

Another problem of the bone cements known so far is that residual monomer which is always contained therein as well as other additives, e.g. the stabilizer hydroquinone (toxicity class 3) and the accelerator N,N-dimethyl-p-toluidine (toxicity class 2), may dissolve out, thus causing damage.

Furthermore, the shrinkage resulting from polymerization may have a disadvantageous effect which may, in the end, lead to a loosening of the prosthesis.

SUMMARY OF THE INVENTION

The object of the invention is to avoid current polymerization-linked components or effects and to simultaneously give the bone cement long-term stability, bioactivity and chemical stability.

The inventive method for the production of a bone cement solves the aforesaid problems by completely avoiding polymerization itself during the formation of the bone cement. According to the invention, said method consists in that 15 to 50% by weight of a monomer-free polymethylmethacrylate (PMMA) whose average molar mass ranges between 3,000 and 200,000 daltons and whose acid value ranges between 10 and 350 mg KOH per g polymer is mixed with a biocompatible, organic solvent or solvent mixture for the PMMA and 0.05 to 80% by weight of a bioactive, vitreous-crystalline material with a particle size ranging between >20 and 200 μm is added to the mixture while stirring and at a temperature ranging between 10 and 50° C. until a flowable mixture is obtained whose open processing time ranges between 1 and 20 minutes, wherein the vitreous-crystalline material consists of 15–45% by weight CaO, 40–45% by weight $P_2O_5$, 10–40% by weight $ZrO_2$ and 0.7–3.5% by weight fluoride and contains apatite and calcium zirconium phosphate as main crystal phases and a glass phase as an auxiliary component, said main crystal phases jointly making up at least 35% by weight and said auxiliary components making up 5 to 15% by weight.

The mixture can be introduced in the body and set therein at body temperature since no polymerization reaction takes place within said mixture. For this purpose, a PMMA whose acid value has been modified and having a molar mass as indicated above is dissolved in a suitable solvent, e.g. ethyl acetoacetate or mixtures of ethyl acetoacetate with ethanol, which ethanol may contain water up to an amount of 4% by volume. The sticky, flowable component obtained in this way is now mixed with a powder mixture of the vitreous-crystalline material and optionally of additional, totally or partially resorbable and/or long-term stable bioceramic and optionally $TiO_2$. The particle size of the powdery components ranges between >20 μm and 200 μm. As a result of the aforesaid procedure, a flowable, sprayable and spreadable mass is obtained ex vivo, which can be processed during a period of several minutes, e.g. 1–10 min, depending on the amount of powder contained therein.

DETAILED DESCRIPTION

It is preferred that a polymethylmethacrylate be used in an amount ranging between 30 and 35% by weight.

The average molar mass of the PMMA may preferably range between 20,000 and 80,000 daltons.

The acid value may preferably range between 25 and 65 mg KOH per g polymer. In this context, the acid value indicates the amount of KOH in mg required to neutralize 1 g of the polymer sample. It is an essential criterion as the number of free carboxyl groups of the polymer is important with regard to bonding to the metal components.

The acrylate whose acid value has been modified can be produced from methylmethacrylate and methacrylic acid by means of a suspension polymerization, wherein the ratio of the molar masses has to be selected such that the desired acid value is achieved. Alternatively, the polymer whose acid value has been modified can be obtained by alkaline saponification of a polymer consisting of methylmethacrylate and ethylmethacrylate. The ethylmethacrylate makes up 2 to 10 mols, preferably 6 mols.

A preferred vitreous-crystalline material contains 23–39% by weight CaO, 40–45% by weight $P_2O_5$, 20–35% by weight $ZrO_2$ and 1–3% by weight fluoride and contains apatite and calcium zirconium phosphate as main crystal phases and a glass phase as an auxiliary component, said main crystal phases jointly making up at least 35% by weight and said auxiliary components making up 5 to 15% by weight.

Another preferred vitreous-crystalline material contains 23–39% by weight CaO, 40–45% by weight $P_2O_5$, 20–35% by weight $ZrO_2$ and 1–3% by weight fluoride and in addition 0.1–6% by weight $Na_2O$ and contains apatite and calcium zirconium phosphate as main crystal phases and a glass phase as an auxiliary component and a sodium zirconium phosphate phase as an additional auxiliary component. Said main crystal phases jointly make up at least 35% by weight and each of said auxiliary components can make up 5 to 15% by weight.

In addition, the vitreous-crystalline material according to the invention may contain 0.1 to 6% by weight magnesium oxide and/or potassium oxide and in addition also the corresponding phases.

The amount of $Na_2O$, MgO and/or $K_2O$ contained preferably ranges between 1 and 6% by weight. The corresponding secondary crystal phase, i.e. sodium zirconium phosphate, preferably makes up 5 to 10% by weight.

The vitreous-crystalline material is produced by preparing a mixture of suitable substances, i.e. with 15–45% by weight CaO, 40–45% by weight $P_2O_5$, 10–40% by weight $ZrO_2$ and 0.7–3.5% by weight fluoride. Advantageously, the fluoride is added in the form of $CaF_2$. The aforesaid components are combined with one another, subjected to suitable, mostly multi-stage thermal treatment programmes (holding stages in the range between 400 and 1,500° C.) and finally melted at between 1,550 and 1,650° C. in a suitable crucible material, preferably consisting of a Pt/Rh alloy. The melt is poured and once it has solidified the mass is cooled down to room temperature in air (spontaneous cooling) or in a cooling furnace, depending on its intended use. Finally, the material is ground.

In general, the terms "glass ceramic" and "vitreous-crystalline material" used herein cannot always be clearly defined. Both crystalline and vitreous and/or X-ray amorphous phases are provided in a thoroughly mixed state. It is of no importance for the present invention whether one phase is located adjacent to the other or one phase encloses the other.

The term "main crystal phase" as used herein refers to a crystalline phase which is contained in at least twice the amount of a secondary phase, concentrations of approximately 15% and below, preferably below 10% by weight, being referred to as secondary phases.

The bioceramic material which may be used in addition to said vitreous-crystalline material is preferably selected from among materials containing sodium, potassium, calcium, magnesium, hydroxyl ions or hydroxyl components, fluoride, silicate and/or ortho-phosphate. A preferred bioceramic material contains crystalline phases of $Ca_2KNa(PO_4)_6$ and an inner open-pore structure. By adding resorbable bioceramics, porous structures can be achieved which may have osteoconductive effects and at the same time act as a support. The gradual dissolution of the bioceramic particles depends on the structure thereof and can be adjusted as desired. Advantageous materials include e.g. a material produced according to DE 19744809 C1 and/or materials containing $Ca_2KNa(PO_4)_6$ or similar phases. If long-term stable, bioactive ceramics or glass ceramics are used instead, one of the crystalline phases should be apatite. An advantageous glass ceramic is based on apatite/wollastonite according to DD 247574A3.

The particle size (grain size) may preferably range between 25 and 160 µm, preferably 25 and 90 µm. The particle size is measured by means of laser granulometry.

In order to obtain a material with higher X-ray density, it is recommended that a material be admixed to the bone cement composite according to the invention which consists of the following components or contains the same in amounts above 30% by weight: $CaZr_4(PO_4)_6$ and/or $CaTi_4(PO_4)_6$. It is of no importance for the intended use of the material whether calcium zirconium phosphate and/or calcium titanium orthophosphate is provided in an amorphous or rather in the more typical crystalline form.

Further, it has been found that $TiO_2$ may be added as an additional inorganic filler, preferably in an amount ranging between 0.1 and 10% by weight in relation to the total weight of the cement and preferably in the form of its modification rutile, and that considerably higher strengths can be achieved thereby.

Due to its structure, the cement also has a certain stickiness with respect to metal oxides and as a result adheres better to the outer oxide layer of e.g. ceramic surfaces or implants made of titanium alloys.

The inventive method may include the incorporation of medicines, e.g. antibiotics, which advantageously may be added to individual components of the mixture, e.g. the bioceramic material, or may be added into the mixture as a separate component. Preferably, gentamicin is added in an amount ranging between approximately 0.5 and 2% by weight, preferably 0.8 and 1.3% by weight, relative to the total weight of the cement.

A particular advantage of the cement according to the invention consists in that it is a zinc-free and monomer-free cement which is easy to mix, whose thixotropy and/or pore size is adjustable and which does not release any toxic substances into the surrounding tissue. The cement according to the invention is zinc-free, which is particularly advantageous since zinc in higher concentrations may have a toxic effect (Contzen et al., Grundlagen der Alloplastik mit Metallen und Kunststoff [Fundamentals of Alloplasty with Metals and Plastics], Thieme Verlag Stuttgart, 1967, p. 56). In particular, the cement has absolutely no toxic effect since zinc and monomers as well as the usual stabilizers and accelerators are avoided. Another advantage consists in that the cement does not set during the mixing process, i.e. in 1 to 10 minutes, preferably 4–5 minutes, but remains plastic during 3 to 8 minutes on average.

All the aforesaid features enable the cement to be evenly spread on the implant surface and on the bone, resulting in a uniform thickness of the layer applied thereto. In this way, a uniform contact between the implant and the bone brought about by the cement can be ensured. Processing errors occur much more seldom.

Another advantage is the stability of shape and volume of the bone cement according to the invention, i.e. in that shrinkage processes may be essentially reduced. An optimization leads to results distinctly below 1%.

Furthermore, an essential advantage of the method according to the invention is that the conventional polymerization reaction is avoided, thereby avoiding the rise in temperature which is otherwise inevitably caused by the exothermal reaction, and thus damage to surrounding cells by temperatures above approximately 50–60° C. is ruled out completely (on the disadvantages of such polymerization reactions see Liebergall et al., Clin. Orthop. 1998 April (349)242–248 and Sturup et al., Acta Orthop. Scand. 1994 February 65(1), 20–23).

By means of the molecular weight of the PMMA and the number of active groups (acid value), the size of the pores can also be adjusted, e.g. pores ranging between 1 µm and 159 µm can be achieved.

By using the bioactive vitreous-crystalline material and, if appropriate, other bioceramic powders, optimal hollow spaces for the growing-in of cells may be created as a consequence of the dissolution of powder particles.

The setting process is brought about by the formation of chelate compounds. These may be formed by partially soluble components of the ceramics.

Furthermore, the method may be made advantageous by adjusting the porosity of the hardened cement by means of a percentage of resorbable bioceramic material which may range between 5 and 80% by weight, preferably 10 and 40% by weight, in relation to the total weight of the bone cement. The viscosity of the mouldable and sprayable cement is adjusted by varying the percentage of the components of the mixture and/or the molecular weight of the PMMA.

The stability characterised by the modulus of elasticity (determined from measuring bending strength) may be adjusted in a range from 5 to 50 MPa by varying the ratio of long-term stable vitreous-crystalline or resorbable inorganic material and dissolved polymer.

The invention further relates to a bone cement kit based on polymethylmethacrylate characterized by the following components provided separate of one another:

15 to 50% by weight of a monomer-free polymethylmethacrylate (PMMA) whose average molar mass ranges between 3,000 and 200,000 daltons and whose acid value ranges between 10 and 350 mg KOH per g polymer;

5 to 40% by weight of a biocompatible organic solvent or solvent mixture for the PMMA;

0.05 to 80% by weight of a bioactive vitreous-crystalline material with a particle size ranging between >20 and 200 μm, which vitreous-crystalline material consists of 15–45% by weight CaO, 40–45% by weight $P_2O_5$, 10–40% by weight $ZrO_2$ and 0.7–3.5% by weight fluoride and contains apatite and calcium zirconium phosphate as main crystal phases and a glass phase as an auxiliary component, said main crystal phases jointly making up at least 35% by weight and said auxiliary components making up 5 to 15% by weight.

In addition, the bone cement kit may contain components provided separately or as a mixture with component c) selected from the group consisting of $TiO_2$, X-ray contrast media, such as $CaZr_4(PO_4)_6$ or $CaTi_4(PO_4)_6$, a resorbable bioceramic material with crystalline phases of $Ca_2KNa(PO_4)_6$ and an inner open-pore structure, a long-term stable glass ceramic based on apatite/wollastonite (according to DD 247574) or mixtures thereof.

The biocompatible solvent included in the bone cement kit according to the invention is ethyl acetoacetate or a mixture of ethyl acetoacetate with ethanol, which ethanol may contain water up to an amount of 4% by volume. Preferably, it is ethyl acetoacetate.

The kit according to the invention is sterilized using ethylene oxide or by means of radiation and is provided in a sterilized form.

The kit may further contain medicinal components, which are either mixed with the individual components or provided separately, particularly antibiotics.

The invention will hereinafter be explained in more detail by means of examples. All percentages are by weight.

EXAMPLE 1

Production of the Vitreous-crystalline Material Apatite/CZP1

A mixture having the following composition is prepared (Code: Apatite/CZP1):
25.88 CaO
28.44 $ZrO_2$
43.68 $P_2O_5$
5.00 $CaF_2$.

In doing so, the amount of CaO can be added in the form of 62.79 $CaHPO_4$ and the required amount of $P_2O_5$ can be incorporated in the form of 10.51 ml of an 85% $H_3PO_4$. First, $CaHPO_4$, $ZrO_2$ and $CaF_2$ are thoroughly mixed, then the phosphoric acid is added, the mixture is left to react and subsequently ground in a mortar, the process including holding stages at 120° C. and 170° C. lasting 4 hours each and intended to dry the product. The reaction mixture obtained in this way is filled into a Pt/Rh crucible, heated up to 400° C., held at this temperature for 1 hour, heated up to 800° C., held at this temperature for 1 hour, cooled and ground in a mortar. The material pre-treated in this way is now melted in a Pt/Rh crucible, the melting process including holding times of 15 min at 800, 1,000, 1,300, 1,500 and finally 1,600° C. respectively, and poured onto a steel plate (room temperature).

Once the melt had solidified, part of the material obtained was milled in an agate mill and particles below 43 μm were separated by sieving and analyzed by means of X-ray diffractography. The result (X-ray diffractogram) shows that the crystal phases apatite (fluoroapatite/hydroxyapatite) and calcium zirconium phosphate [$CaZr_4(PO_4)_6$] are clearly detectable in the vitreous-crystalline product. The remaining part of the solidified melt is comminuted until a particle size of >20 to 200 μm is achieved.

EXAMPLE 2

Production of the Vitreous-crystalline Material Apatite/CZP2

A mixture is prepared according to the instruction of Example 1, except that sodium oxide is added as an additional component (Code: Apatite/CZP2). Specifically, the following components are mixed:
59.93 $CaHPO_4$
27.10 $ZrO_2$
3.42 $Na_2O$
5.00 $CaF_2$ and
9.56 ml of an 85% $H_3PO_4$.

Processing was done as in Example 1. At the end of the last temperature holding stage, the melt was poured out of the crucible onto a steel plate.

Once the melt had solidified, part of the material obtained was milled in an agate mill and particles below 43 μm were separated by sieving and analyzed by means of X-ray diffractography. The result (X-ray diffractogram) shows that the crystal phases apatite (fluoroapatite/hydroxyapatite) and calcium zirconium phosphate [$CaZr_4(PO_4)_6$] and sodium zirconium phosphate [$NaZr_2(PO_4)_3$] are detectable in the vitreous-crystalline product.

The remaining part of the solidified melt is comminuted until a particle size of >20 to 200 μm is achieved.

EXAMPLE 3

Coefficients of Expansion of Apatite/CZP1

A vitreous-crystalline material according to Example 1 was produced (Apatite/CZP1). The material was milled in a mill lined with zirconium oxide until a $D_{50}$-value of 8 μm was achieved. The ground material was combined with a 5% polyvinylalcohol (PVA) solution, the ratio of ground material to PVA solution being 90 to 10% by weight, and the mixture was compression-moulded into a rod applying a force of 4.7 kN. The resulting compact is sintered at a temperature of 1,050° C.

Then, the thermal coefficient of expansion (CE) of the relatively dense moulded body obtained in this way is determined:

| | |
|---|---|
| CE in the range of 27–400° C. | $1.90 * 10^{-6}$ degrees Celsius$^{-1}$ |
| CE in the range of 50–400° C. | $1.86 * 10^{-6}$ degree Celsius$^{-1}$ |
| CE in the range of 30–300° C. | $1.45 * 10^{-6}$ degree Celsius$^{-1}$ |
| CE in the range of 30–400° C. | $1.88 * 10^{-6}$ degree Celsius$^{-1}$ |
| CE in the range of 30–600° C. | $2.6 * 10^{-6}$ degree Celsius$^{-1}$ |
| CE in the range of 30–800° C. | $3.2 * 10^{-6}$ degree Celsius$^{-1}$ |

EXAMPLE 4

Chemical Stability of Apatite/CZP1 in the Alkaline Range

A vitreous-crystalline material according to Example 1 is produced (Apatite/CZP1). Subsequently, the material is ground in a mortar until a particle size fraction of 315–400 µm is obtained.

The chemical stability of the granulated material obtained in this way was compared to those of a basic glass ($Ap40_{glass}$) and a glass ceramic made from said basic glass and based on apatite and wollastonite ($Ap40_{cryst.}$) [i.e. with a chemical composition corresponding to (% by weight): 44.3 $SiO_2$; 11.3 $P_2O_5$; 31.9 CaO; 4.6 $Na_2O$; 0.19 $K_2O$; 2.82 MgO and 4.99 $CaF_2$].

First, the specific surface areas according to BET were determined using krypton as measuring gas. The following results were obtained:

| | |
|---|---|
| Apatite/CZP1: | 0.364 m$^2$/g |
| $Ap40_{glass}$: | 0.018 m$^2$/g |
| $Ap40_{cryst.}$: | 0.055 m$^2$/g. |

It can be seen that the vitreous-crystalline material used in the bone cement according to the invention has a certain open porosity compared to the basic glass and the glass ceramic made therefrom. These differences were taken into account in the solubility tests by adjusting the ratio of surface (sample) to volume of solvent (TRIS HCl buffer solution) to a constant value of 5 cm$^{-1}$.

The solvent used was 0.2M TRIS HCl buffer solution, pH=7.4, at 37° C. The samples were stored therein for 120 hours at a temperature of 37° C. Then the samples' total solubility was determined by determining the individual ions (Ca, P, Zr) in the solution by means of an ICP measurement. The following results were obtained:

| | |
|---|---|
| Apatite/CZP1: | 4.1–5.1 mg/l |
| $Ap40_{glass}$: | 318–320 mg/l |
| $Ap40_{cryst.}$: | 75.2–82.0 mg/l. |

The above values impressively demonstrate the high chemical stability of the novel material used in the bone cement according to the invention under simulated physiological conditions, which is a known method for determining long-term stability in vitro.

EXAMPLE 5

Chemical Stability of Apatite/CZP1 in the Acid Range

The same procedure as in Example 4 is carried out, except that 0.2M TRIS HCl buffer solution having a pH value of 6.0 and a temperature of 37° C. is used for measuring. In this way, an infection during the wound healing process or at a later stage causing the pH value to fall from the physiological value of 7.4 down into the acid range can be simulated.

The following total solubility values were determined by means of ICP:

| | |
|---|---|
| Apatite/CZP1: | 16–19 mg/l |
| $Ap40_{glass}$: | 505–518 mg/l |
| $Ap40_{cryst.}$: | 117–125 mg/l. |

The above values impressively demonstrate the high chemical stability of the material used for the invention under simulated conditions corresponding to those during an inflammation reaction. According to the test results, the absolute solubility values of the material according to the invention increase to a much smaller extent than those of the basic glass and/or the glass ceramic based on apatite/wollastonite which rise quite dramatically.

EXAMPLE 6

Production I of the Bone Cement

The starting material was a monomer-free polymethyl-meth-acrylate (PMMA) whose acid value had been modified and whose average molar mass was approx 100,000. 3 g of this PMMA (acid value 62 mg KOH/g) was added into 7 g of a mixture of 50 parts of ethanol (abs.) and 60 parts of ethyl acetoacetate and processed into a solution of 30% by weight by stirring. Then a mixture of vitreous-crystalline material and/or bioceramic material was added at room temperature (18–25° C.) and stirred until a homogeneous mixture was obtained.

The total mixture obtained in this way had a creamy consistency and was processed as bone cement within one of the respective setting times.

The table below shows the respective data for the individual components as percentages of the total mixture. "Polymer mixture" means polymer+solvent.

The bioceramics and/or the vitreous-crystalline material added had an average particle size of 50–200 µm. The following materials were used:

| | | |
|---|---|---|
| Resorbable bioceramic (DE 19744809) | 56–90 µm | 21% by weight |
| Apatite/CZP2 (Example 2) | 71–100 µm | 21% by weight |
| Tetracalcium phosphate | 20 µm | 21% by weight |
| $TiO_2$ | | 10.4% by weight |

The material was easy to mix and had a sticky-creamy consistency. It was sprayable and water-resistant. Pore diameters of up to 150 µm were achieved. The bending strength was 12.2 MPa.

EXAMPLE 7

Production II of the Bone Cement

The starting material was a monomer-free polymethyl-meth-acrylate (PMMA) whose acid value had been modified and whose average molar mass was approx. 100,000. 3 g of this PMMA (acid value 62 mg KOH/g) was added into 7 g of a mixture of 60 parts of ethanol (96%) and 50 parts of ethyl acetoacetate and processed into a solution of 30% by weight by stirring. Then a mixture of bioceramic material was added at room temperature (18–25° C.) and stirred until a homogeneous mixture was obtained.

The total mixture obtained in this way had a creamy consistency and was processed as bone cement within one of the respective setting times.

The table below shows the respective data for the individual components as percentages of the total mixture.

The added bioceramics had an average particle size of 50–200 μm. The following bioceramics were used:

| | | |
|---|---|---|
| Resorbable bioceramic (DE 19744809) | 56–90 μm | 21% by weight |
| Apatite/CZP2 (material of Example 2) | 71–100 μm | 21% by weight |
| Tetracalcium phosphate | 20 μm | 21% by weight |
| $TiO_2$ | | 10.4% by weight |

The material was easy to mix and had a sticky-creamy consistency. It was sprayable and water-resistant. Pore diameters of up to 150 μm were achieved. The bending strength was 10.4 MPa.

Now that the invention has been described:

What is claimed is:

1. A bone cement kit based on poly-methylmethacrylate comprising the following components provided separate of one another:
    a) 15 to 50% by weight, relative to the total weight of the bone cement, of a monomer-free polymethylmethacrylate (PMMA) whose average molar mass ranges between 3,000 and 200,000 daltons and whose acid value ranges between 10 and 350 mg KOH per g polymer;
    b) 10 to 40% by weight, relative to the total weight of the bone cement, of a biocompatible organic solvent or solvent mixture for the PMMA; and
    c) 0.05 to 80% by weight, relative to the total weight of the bone cement, of a bioactive, vitreous-crystalline material with a particle size ranging between >20 and 200 μm, the vitreous-crystalline material comprising:
    15–45% by weight CaO,
    40–45% by weight $P_{2O5}$,
    10–40% by weight $ZrO_2$ and
    0.7–3.5% by weight $CaF_2$,
    relative to the total weight of the vitreous-crystalline material, and further comprising:
    apatite and calcium zirconium phosphate as main crystal phases and a glass phase as an auxiliary component, wherein said main crystal phases of the vitreous-crystalline material jointly making up at least 35% by weight and said auxiliary component making up 5 to 15% by weight.

2. The bone cement kit according to claim 1 wherein the biocompatible solvent used is ethyl aceto-acetate or a mixture of ethyl acetoacetate with ethanol.

3. The bone cement kit according to claim 2 wherein the biocompatible solvent is ethyl aceto-acetate.

4. The bone cement kit according to claim 1 wherein said kit additionally comprises a component chosen from:
    $TiO_2$,
    X-ray contrast media,
    a resorbable bioceramic material,
    a long-term stable glass ceramic based on apatite/wollastonite, or
    mixtures thereof.

5. The bone cement kit according to claim 4 wherein the resorbable bioceramic material comprises crystalline phases of $Ca_2KNa(PO_4)_2$ and an internal open-pore structure.

6. The bone cement kit according to claim 4 wherein the X-ray contrast media is chosen from $CaZr_4(PC_4)_6$ or —$CaTi_4(PO_4)_6$.

7. The bone cement kit according to claim 1 wherein the polymethylmethacrylate is used in an amount ranging between 30 and 35% by weight.

8. The bone cement kit according to claim 1 wherein the vitreous-crystalline material is a material composed of 23–39% by weight CaO, 40–45% by weight $P_2O_5$, 20–35% by weight $ZrO_2$ and 1–3% by weight fluoride.

9. The bone cement kit according to claim 1 wherein the vitreous-crystalline material comprises 0.1 to 6% by weight $Na_2O$ and the auxiliary component comprises a sodium zirconium phosphate phase.

10. The bone cement kit according to claim 1 further comprising $TiO_2$ as inorganic filler.

* * * * *